United States Patent [19]

Meinert et al.

[11] Patent Number: 5,120,731
[45] Date of Patent: Jun. 9, 1992

[54] STABILIZATION OF PERFLUOROCARBON EMULSIONS, AND PERFLUORINATED HETEROCYCLIC COMPOUNDS USABLE AS EMULSION-STABILIZING ADDITIVES

[75] Inventors: Hasso Meinert; Juergen Mader, both of Ulm; Rudolf Fackler, Senden; Peter Reuter, Ulm-Lehr; Wolfgang Roehlke, Ulm-Maehringen; Monika Gennies; Joachim Baer, both of Ulm, all of Fed. Rep. of Germany

[73] Assignee: Kalie-Chemie AG, Hanover, Fed. Rep. of Germany

[21] Appl. No.: 572,488

[22] Filed: Aug. 27, 1990

[30] Foreign Application Priority Data

Aug. 3, 1989 [DE] Fed. Rep. of Germany ....... 3928692
Dec. 15, 1989 [DE] Fed. Rep. of Germany ....... 3941514

[51] Int. Cl.⁵ .................... A61K 31/535; C07D 265/30
[52] U.S. Cl. .............................. 514/231.5; 514/231.8; 514/316; 544/78
[58] Field of Search ............ 544/78; 514/231.5, 231.8, 514/316

[56] References Cited

U.S. PATENT DOCUMENTS

3,956,293 5/1976 Pavlik .................... 544/85
4,530,926 7/1985 Yokoyama et al. ............ 514/214
4,766,261 8/1988 Bierl .................... 570/179

FOREIGN PATENT DOCUMENTS

77114 4/1983 European Pat. Off.
2171330 8/1986 United Kingdom.

OTHER PUBLICATIONS

Hayashi et al; Chemical Abstract; vol. 109, 1988, #199847d.
Higuchi et al., "Physical Degradation of Emulsions via the Molecular Diffusion Route and the Possible Prevention Thereof", *J. Pharmaceutical Sciences*, 51:459-66 (1962).
Davis et al., "Ostwald Ripening and the Stability of Emulsion Systems: An Explanation for the Effect of an Added Third Component", *J. Colloid and Interface Science*, 80:508-11 (1981).
Kabal'nov et al., "Influence of Nature and Composition of Disperse Phase in Emulsions of Perfluoroorganic Compounds on the Kinetics of the Decrease in Emulsion Dispersity", pp. 20-24 (1986).

*Primary Examiner*—Robert T. Bond
*Assistant Examiner*—Y. N. Gupta
*Attorney, Agent, or Firm*—Foley & Lardner

[57] ABSTRACT

The use of perfluorinated heterocyclic compounds of the general formula I.

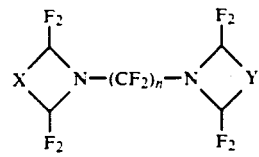

wherein
n represents 2-8,
X and Y represent a $-CF_2OCF_2-$ group, a $-CF_2-CF_2-CF_2-$ group or a $-CF(CF_3)-CF_2-$ group, and
Y is a $-CF_2-O-CF_2-$ group, a $-CF(CF_3)-CF_2-$ group or a $-CF_2-CF_2-CF_2-$ group, or mixtures thereof, is described as emulsion-stabilizing additives in medically usable aqueous emulsions of perfluorocarbons, optionally containing hetero atoms, suitable for use in blood substitutes. The compounds are obtained by electrochemical perfluorination.

20 Claims, No Drawings

STABILIZATION OF PERFLUOROCARBON EMULSIONS, AND PERFLUORINATED HETEROCYCLIC COMPOUNDS USABLE AS EMULSION-STABILIZING ADDITIVES

BACKGROUND OF THE INVENTION

The present invention relates to the use of a group of perfluorinated heterocyclic compounds which contain two heterocycles connected by a perfluoroalkylene chain, as emulsion-stabilizing additives in medically usable aqueous emulsions of perfluorocarbons, optionally containing hetero atoms.

The present invention further relates to mixtures suitable for preparing medically usable aqueous emulsions, of physiologically acceptable perfluorocarbons containing hetero atoms in some cases, which contain perfluorocarbons, containing hetero atoms in some cases, suitable for use as oxygen transfer agents in blood substitutes, and emulsion-stabilizing additives of the above-named group of perfluorinated heterocyclic compounds, as well as medically usable aqueous emulsions of these mixtures, as well as new perfluorinated heterocyclic compounds suitable as emulsion-stabilizing components of perfluorocarbon emulsions.

Saturated perfluorinated organic compounds which consist of carbon and fluorine and can in some cases contain hetero atoms— for example nitrogen or oxygen— in the carbon chain, are called perfluorocarbons. As used herein, the term, "perfluorocarbons," identifies perfluorocarbon compounds, optionally containing hetero atoms. Such compounds are known, for example, from published European patent application Nos. EP 77,114; EP 99,652; and EP 151,697. The perfluorocarbon molecules are outstandingly shielded by a uniform shell of fluorine atoms. Therefore perfluorocarbons are chemically and physically extraordinarily inert, i.e., nontoxic. Due to their extremely low intermolecular forces, perfluorocarbons have a low boiling point in relation to their molecule weights, and an extraordinarily low surface tension. A result of the very weak intermolecular forces is also the ability of the perfluorocarbons to dissolve large amounts of gases, such as oxygen and carbon dioxide. Because of these properties, especially the ability to dissolve oxygen physically and transport it, perfluorocarbons have found application in medicine in the preparation of aqueous perfluorocarbon emulsions transporting oxygen, which can be used, for example, as blood substitutes or as media for organ perfusion and organ storage in transplant surgery.

Perfluorocarbons are hydrophobic substances which are immiscible with water. Therefore they cannot be introduced as such into the blood stream, but only in the form of physiologically acceptable aqueous emulsions. Such emulsions are prepared conventionally with the aid of a physiologically acceptable emulsifier and constitute emulsions of the oil-in-water type.

In addition to good physiological compatibility, e.g., osmotic and oncotic (colloid osmotic) pressures, rheological properties and pH stability similar to normal blood, and a good capacity for dissolving oxygen, it is important in emulsions usable as blood substitutes that they have an appropriate persistence in the blood stream and that they then be eliminated again as completely as possible and without excessive retention in organs. About one week to one month, especially about 2 to 4 weeks, is considered to be a good half-life in the body. Furthermore, it is important that the emulsions have sufficient stability against any growth of the oil phase particles.

Due to their chemical inertness, perfluorocarbons are virtually not metabolized in the body and are eliminated in unaltered form in the breath or through the skin. The rate of elimination of individual perfluorocarbons varies greatly and can run from a few days to a number of years. The rate of elimination of the individual substances depends greatly on their vapor pressure and on their solubility in low-polar media, since the rate of migration of the perfluorocarbons through the alveolar membranes depends on these parameters.

The critical temperature of dissolution in n-hexane (=CTSH) can serve as a measure of the lipophilia of the perfluorocarbons, that is, the temperature at which the perfluorocarbon in question dissolves in an equal amount of n-hexane. The determination of the CTSH of a perfluorocarbon is therefore an in-vitro test method which represents a good indication of the persistence of the perfluorocarbon in the body.

An adequate lipophilia and a sufficiently high vapor pressure are advantageous toward a satisfactory exhalation rate.

The chief reason for the growth of droplets in emulsions is to be found in the coalescence of droplets. This can generally be suppressed by the use of emulsifiers which form a barrier at the oil-water interface and reduce the boundary surface tension. Another, less striking cause of the aging of emulsions by particle growth can lie in a molecular diffusion known as Ostwald ripening: molecules diffuse from small droplets of the oil phase through the aqueous phase into larger droplets of the oil phase. This molecular diffusion can also take place in the presence of emulsifiers that are active against coalescence. The phenomenon of molecular diffusion occurs all the more with the increase of the vapor pressure of the particular perfluorocarbons.

Perfluorocarbons which have a half-life in the body of one week to one month are preferred as oxygen transfer components of emulsions usable as blood substitutes. An input of large amounts of substances of long half-life is not expedient, since they can lead to an undesirably long retention of the substances in the body. Perfluorocarbons having a half-life of less than a week are not desirable either. Perfluorocarbons having a suitable half-life in the body are generally perfluorocarbons which are liquid at body temperature, e.g., substances with a boiling point ranging from 130 to 200° C., and with a correspondingly high vapor pressure range and molecular weights ranging from 450 to 600, especially 460 to 550. These substances, however, have the disadvantage that their emulsions have a strong tendency toward particle growth by molecular diffusion.

Perfluorodecalin [Dekalin®= decahydronaphthalene] is such a perfluorocarbon, which is clinically used in emulsions serving as blood substitutes on account of its good oxygen transporting ability, its non-toxicity and its satisfactory rate of elimination. Unfortunately, this substance does not provide emulsions that are stable over a long period at room temperature. Attempts have already been made to achieve more stable emulsions in which, instead of perfluorodecalin, which is made up only of carbon and fluorine, a perfluorocarbon mixture of perfluorodecalin and an acyclic perfluorocarbon is used, which does contain a nitrogen atom and which has a certain polarity on account of the nitrogen atom contained in the molecule, e.g., perfluorotripropylamine or perfluorotributylamine. For the achievement of a useful improvement of the stability of the emulsion it was necessary to replace about-one-third of the perfluorodecalin with perfluorotripropylamine. Thus, the Fluosol-DA ®20% (Green Cross Corporation) sold as a blood substitute is an aqueous emulsion which contains 14% (G/V) perfluorodecalin and 6% (G/V) perfluorotripropylamine as well as physiologically acceptable emulsifiers and other adjuvants. This product too does not have satisfactory long-term stability. Also, the high content of polar, higher-boiling, nitrogenous perfluorocarbon with an undesirably long half-life in the body of about 65 days, is disadvantageous.

SUMMARY OF THE INVENTION

The object of the present invention is to provide perfluorocarbon mixtures usable for preparing aqueous perfluorocarbon emulsions of improved stability suitable for medical purposes, especially as a blood substitute.

These and other objects of the invention are achieved by providing a method of stabilizing an aqueous perfluorocarbon emulsion suitable for use as a blood substitute, said method comprising incorporating in said emulsion an effective emulsion stabilizing amount of at least one perfluorinated heterocyclic compound corresponding to the formula I:

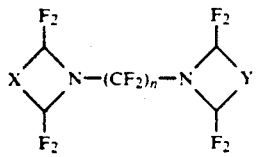

wherein n represents an integer from 2 to 8;

X represents a —$CF_2$—O—$CF_2$— group, a —$CF_2C$-$F_2$—$CF_2$l3 group, or a —CF($CF_3$)—$CF_2$— group, and Y represents a —$CF_2$—O—$CF_2$— group, a —CF($CF_3$)—$CF_2$— group, or a —$CF_2$—$CF_2$—$CF_2$— group.

According to a further aspect of the invention, the objects are achieved by providing a composition of matter suitable for preparing medically useful aqueous emulsions, said composition comprising, in admixture, a physiologically acceptable perfluorocarbon suitable for use as an oxygen carrier in a blood substitute, and at least one perfluorinated heterocyclic compound corresponding to the formula I:

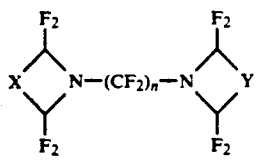

wherein n represents an integer from 2 to 8;

X represents a —$CF_2$—O—$CF_2$— group, a —$CF_2$—$CF_2$—$CF_2$— group, or a —CF($CF_3$)—$CF_2$— group, and Y represents a —$CF_2$—O—$CF_2$— group, a —CF($CF_3$)—$CF_2$— group, or a —$CF_2$—$CF_2$—$CF_2$— group.

In a further aspect of the invention, the objects are achieved by providing a perfluorinated heterocyclic compound corresponding to the formula I':

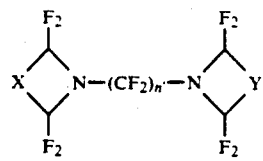

wherein n' represents an integer from 4 to 8;

X represents a —$CF_2$—O—$CF_2$— group, a —$CF_2$—CFhd 2—$CF_2$— group, or a —CF($CF_3$)—$CF_2$— group, and Y represents a —$CF_2$—O—$CF_2$— group, a —CF($CF_3$)—$CF_2$— group or a —$CF_2$—$CF_2$—$CF_2$— group.

DETAILED DESCRIPTION OF PREFERRED EMBODIMENTS

It has now been found that the undesired growth, due to molecular diffusion, of the perfluorocarbon phase particles in aqueous emulsions of perfluorocarbons usable as oxygen carriers in blood substitutes can be inhibited by the addition of compounds of a group of perfluorocarbons which are characterized in their chemical structure by the fact that they contain two perfluorinated rings (each containing one nitrogen atom with a tertiary bond to 3 carbon atoms), which are linked by a perfluoroalkylene chain, and that the addition of these compounds to perfluorocarbons results in a good emulsifiability of the resulting perfluorocarbon mixtures and a high stability of aqueous emulsions of these mixtures.

A work by Hayashi et al. (Chem. Express 1988, 3, 191-194, see Chem. Abstr. Vol. 110, 75255k (1989)) discloses perfluorinated heterocyclic ethylene diamines and propylene diamines which are proposed as inert fluids for use in the electronics industry. However, no kind of application of these compounds in medically usable aqueous emulsions is known.

The subject matter of the present invention is the use of perfluorinated heterocyclic compounds of the general formula I,

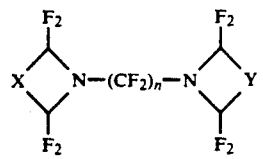

wherein n represents an integer from 2 to 8;

X represents a —$CF_2$—O—$CF_2$— group, a —$CF_2$—$CF_2$—$CF_2$— group or a —CF($CF_3$)—$CF_2$— group, and Y is a —$CF_2$—O—$CF_2$— group, a CF($CF_3$)—$CF_2$— group or a —$CF_2$—$CF_2$—$CF_2$— group, or mixtures thereof as emulsion-stabilizing additives in medically usable aqueous emulsions of perfluorocarbons, optionally containing hetero atoms, suitable for use in blood substitutes.

Compounds of formula I which are preferred for this purpose are those in which n represents from 3 to 6, especially 3 or 4.

The invention also relates to perfluorocarbon mixtures suitable for preparing medically usable aqueous perfluorocarbon emulsions having improved stability, which contain perfluorocarbons (optionally containing hetero atoms), which are suitable for use as oxygen carriers in blood substitutes, with compounds of formula I added, and aqueous emulsions containing these perfluorocarbon mixtures.

To achieve an effective improvement of the stability of the emulsions, amounts of 1–20, preferably 2.5 to 10, percent by weight, of the total perfluorocarbon content of the emulsions can be used. Thus, amounts of 0.5 to 2 grams of the compounds of formula I in 100 ml of emulsion are sufficient for achieving an effective improvement of the stability of the emulsions by inhibiting the particle growth due to molecular diffusion.

It has furthermore been found that, by adding compounds of formula I in accordance with the invention, to aqueous perfluorocarbon emulsions, the boundary surface tension between the perfluorocarbon phase and water is reduced.

On the basis of this phenomenon it is assumed that the compounds of formula I accumulate on the surface of the perfluorocarbon particles and produce their diffusion-inhibiting effect there.

The compounds of formula I are suitable for stabilizing aqueous emulsions of those perfluorocarbons which tend, on the basis of their physical properties in aqueous emulsions toward particle growth due to molecular diffusion. These include the perfluorocarbons suitable as oxygen carriers in blood substitutes, which are characterized by human body retention half-life of between one week and one month, preferably 2 to 3 weeks. These include perfluorocarbons which are liquid to waxy at standard temperature and whose boiling points range from 130 to 200° C., especially from 130 to 180° C. Such perfluorocarbons can have molecular weights ranging from 450 to 600, preferably 460 to 550. These perfluorocarbons include not only cyclic and open-chain compounds consisting only of fluorine and carbon, or cyclic compounds substituted by perfluoroalkyl moieties, but also cyclic compounds containing hetero atoms, e.g., 1 to 4 hetero atoms, especially nitrogen and/or oxygen, optionally substituted by perfluoroalkyl moieties. The cyclic compounds may have a monocyclic or a bicyclic structure. Perfluorodecalin (= perfluorodecahydronaphthalene) is given as a preferred example of a substance free of hetero atoms. Examples of substances containing hetero atoms include perfluorocyclohexylmorpholine and mixtures thereof with perfluoro-n-hexylmorpholine, which are described in a copending patent application, and can be obtained by electrochemical fluorination of morpholinocyclohexene-(1) produced by reacting morpholine with cyclohexanone under the conditions stated below for preparing the compounds of formula I.

The invention furthermore relates to new perfluorinated heterocyclic compounds corresponding to the formula I':

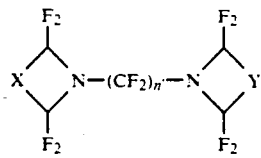

wherein
n' represents 4–8,
X is a —CF$_2$—O—CF$_2$— group, a —CF$_2$CF$_2$—CF$_2$— group or a —CF(CF$_3$)—CF$_2$— group, and
Y is a —CF$_2$—O—CF$_2$— group, a —CF(CF$_3$)—CF$_2$— group, or a —CF$_2$—CF$_2$—CF$_2$— group,
as well as the production thereof.

The new compounds of formula I' have a good ability to dissolve gases such as oxygen and carbon dioxide; they are physiologically inert, and they are characterized by an especially good emulsifiability and a high stability of the aqueous emulsions containing them. Because of their properties, the compounds according to the invention are, for example, suitable as additives for preparing medically usable aqueous emulsions, which can be used, for example, as blood substitutes or perfusion agents.

Furthermore, the compounds are also suitable for use in other technical areas in which nontoxic and chemically inert, liquid or wax-like substances are needed, or inert substances with a capacity for dissolving gases are needed. The compounds of formula I' and their mixtures are suitable, for example, as inert coolants, lubricants, sealing liquids, and hydraulic liquids, insulation media in electrical engineering, as well as media for vapor-phase soldering or as additives to agents for the above-mentioned purposes. Compounds of formula I' having a waxy to solid consistency at room temperature are suitable as inert, temperature-stable lubricants and sealing agents which can be used over a wide temperature range. Due to their capacity for absorbing gases, the compounds of formula I and their mixtures are suitable as inert media for the diffusion of gases between different phases. Thus, the compounds can also be used in processes for industrial separation of gases, for example, the separation of gases by dialysis in which the compounds can serve as an inert exchange phase.

Compounds of formula I can be obtained by fluorinating compounds of general formula II

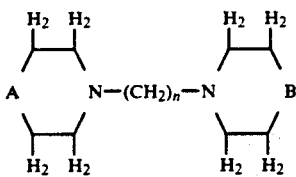

wherein
n has the above meaning,
A represents oxygen or a —CH$_2$— group, and
B is oxygen or a —CH$_2$— group,
by known methods. Thus, the compounds can be prepared by electrochemical fluorination by electrolyzing solutions of the corresponding compounds of formula II in liquid hydrogen fluoride. It is desirable to use for the process solutions of 4 to 30 wt.-%, preferably 5 to 10 wt.-%, of a compound of formula II in liquid hydrogen fluoride. The electrolysis advantageously takes place at temperatures between −25 and +10° C., preferably −5 and +5° C.; at an anode current density of 2 to 30 mA/cm², and at a cell voltage of 3 to 10 volts, preferably 4 to 8 volts.

For further processing, the raw reaction product settling as a heavy phase on the bottom of the electrolysis cell is separated and, to decompose any partially fluorinated by-products, it is subjected to a treatment with an alkali metal or alkaline earth metal base, especially an alkali metal or alkaline earth metal hydroxide, in the presence of water and, if desired, of a lower aliphatic primary or secondary amine, at an elevated temperature sufficient to decompose any partially fluorinated by-products. This process step can be performed under known reaction conditions, e.g., by methods analogous to those described in published European Patent Application Nos. EP 99,652 and EP 151,697. It is especially preferred to treat the raw reaction product with a 6× to 10× normal aqueous alkali metal hydroxide solution, especially a potassium hydroxide solution, and a lower aliphatic amine at elevated temperature, preferably the boiling temperature of the reaction mixture. The reaction mixture can be heated at boiling with refluxing, for example, for a period ranging from several hours up to as many as 8 days. Suitable lower aliphatic amines are lower aliphatic primary or secondary amines or diamines which are liquid at room temperature, preferably secondary amines such as dialkylamines with up to 5 carbon atoms in their alkyl moieties, hexamethylenediamine or even cyclic amines such as piperidine. It is preferred, for example, to use a dibutyl amine such as diisobutylamine.

The compounds of formula I or their mixtures can be separated from the reaction mixture using known techniques, e.g. fractional distillation or preparative gas chromatography.

The compounds separated from the reaction mixture by fractional distillation are free of non-perfluorinated products. However, they may still contain also perfluorinated, and therefore chemically and physiologically inert, by-products. In particular they can contain perfluorinated by-products which have a molecular weight similar to that of the principal product and consequently boil in the same temperature range as the principal product. The presence of such perfluorinated by-products, however, does not impair the use of the compounds in accordance with the invention, so that products purified by distillation can generally be used without further purification.

Under the conditions of the electrochemical perfluorination of compounds of formula II, a ring contraction occurs to some extent in compounds containing piperidine rings, so that, in addition to compounds of general formula I, wherein X represents a —CF$_2$—CF$_2$— group, —CF(CF$_3$)—CF$_2$— group, are also obtained to a slight extent.

These isomeric mixtures of compounds of formula I can be used in the same manner as pure compounds of formula I. If desired, the isomeric mixtures can be separated into their individual isomers. The separation of the isomers is advantageously performed by adsorption-desorption on molecular sieves, preferably molecular sieves with a pore size of about 5 to 6 Å. Suitable molecular sieves include, for example, inorganic aluminum silicates, zeolites and silicalites (= silicon dioxides of suitable pore size). Preferably zeolites are used. Inorganic-molecular sieves are generally suitable for separating compounds according to the invention containing only unsubstituted perfluorinated rings from by-products containing perfluoroalkyl substituents. Depending on the size of the perfluoroalkyl substituents, molecular sieves with pore sizes between 5 and 6.5 Å are selected for this purpose. Isomer mixtures can also be separated in a known manner by preparative gas chromatography.

The starting compounds of formula II are known, or can be prepared by known methods or in a manner analogous to known methods.

For example, the starting compounds of formula II can be obtained by reacting, in a known manner, secondary amines corresponding to the formula III:

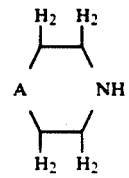

wherein A has the above meaning, with compounds corresponding to the formula VI:

$$E—(CH_2)_n—E \qquad IV$$

wherein E represents halogen, especially chlorine or bromine, or the hydroxyl group, and n has the above meaning.

Compounds of formula II can also be obtained by reacting, in a known manner, dihalides of formula V:

$$E—CH_2—CH_2—A—CH_2—CH_2l3\ E \qquad V$$

wherein A and E have the above meanings, with diamines of the formula VI:

$$NH_2—(CH_2)_n—NH_2. \qquad VI$$

The present invention also relates to medically usable aqueous emulsions. The emulsions in accordance with the invention are oil-in-water type emulsions, which contain for each 100 ml of emulsion, from 5 to 50 grams, especially from 15 to 25 grams, preferably about 20 grams, of perfluorocarbon mixtures containing from 1 to 20 wt.-%, preferably from 2.5 to 10 wt.-%, of compounds of formula I, and a physiologically acceptable emulsifier. It may prove to be especially desirable to add the compounds from the following examples 2b, 2c, 2i or 2j.

Suitable emulsifiers include physiologically acceptable emulsifiers which themselves are nontoxic, have no hemolysis-causing properties, and also do not otherwise have any interaction with components of natural blood, and are completely eliminated from the body or are metabolized with the formation of nontoxic metabolites. Examples of suitable emulsifiers include natural phospholipids such as egg lecithins or soybean lecithins, and albumins. Also suitable are physiologically acceptable nonionic emulsifiers of the ethylene oxide-propylene oxide copolymer type, such as copolymers having a molecular weight in the range from 8,000 to 8,500. Such emulsifiers are commercially available, for example under the trademark Pluronic ®, (Wyandotte Chemicals Corp.) The emulsifiers can be contained in the emulsions according to the invention, in a concentration of, for example, 2 to 7 grams per 100 milliliters of emulsion. Furthermore, the emulsions can also contain additional additives and adjuvants commonly used in blood substitutes, such as salts, and substances serving to establish a physiologically acceptable pH and/or osmotic and oncotic pressure.

The emulsions in accordance with the invention can be prepared in a known manner by conventional emulsifying methods. The emulsification can be performed, for example, by ultrasonic and/ or high-pressure homogenization. The addition of the compounds of formula I containing hetero atoms to the emulsion mixtures not only improves the stability of the emulsion, but also promotes the emulsifiability of the mixture. Thus, stable emulsions can be produced quickly with simple apparatus. The emulsions in accordance with the invention preferably have colloid particle sizes in the range from 50 to 300 nm, and are characterized by a high long-term stability.

The emulsions according to the invention can be used in medicine as oxygen transporting blood substitutes. Furthermore, they can be used as oxygen transporting perfusion solutions, for example to protect exposed organs in surgery, for example for protecting the myocardium against hypoxia in heart surgery, or as perfusion liquids and transporting liquids in transplantation surgery. The emulsions can also find use as adjuvants in diagnostics, for example for ultrasonography and $^{19}F$ NMR tomography. In biotechnology, emulsions according to the invention can be used in oxygen carrying nutrient media, for example for the culture of animal and plant cells, or in the synthesis of interferon.

The following examples are intended to further explain the invention without, however, limiting its scope.

As electrolysis cells for the electrochemical fluorination, cells with nickel electrodes are used which either have a capacity of 300 ml and an anode area of 475 $cm^2$, or a capacity of 960 ml and an anode area of 1530 $cm^2$. The cells are provided with a reflux condenser which is maintained at a temperature between $-15$ and $-20°$ C.

EXAMPLE 1:

Preparation of a mixture of perfluorinated 1,3-dipiperidinopropane, and perfluorinated 1-(3-methylpyrrolidino)-3-piperidinopropane and 1,3-di-(3-methylpyrrolidino)-propane isomeric therewith.

A 10% solution of 1,3-dipiperidinopropane in dried, refrigerated liquid hydrogen fluoride was perfluorinated in an electrolysis cell at a temperature of $+2°$ C., an anode current density of 2.5 to 25 $mA/cm^2$ and a cell voltage of 4.5 to 7.0 V. From time to time dipiperidinopropane dissolved in liquid hydrogen fluoride and spent hydrogen fluoride were replaced to permit continuous operation of the cell. The raw reaction product collecting on the cell bottom was withdrawn from time to time. The raw product was worked up by treating with respective equal volumes of an aqueous 8N potassium hydroxide solution and dibutylamine. The mixture was heated for 8 days with refluxing. Then the mixture was fractionally distilled. In the distillation a main fraction which boiled at 195 to 203° C. was obtained. This fraction consisted of the isomer mixture named in the title and could be used without further purification for the uses mentioned in the foregoing description.

A gas-chromatographic separation of this mixture showed that the mixture contained 58% perfluorinated 1,3-dipiperidinopropane with a boiling point of 191° C., 36% perfluorinated 1-(3-methylpyrrolidino-3-piperidinopropane with a boiling point of 189° C., and 6% perfluorinated 1,3-di(3-methylpiperidino)-propane with a boiling point of 186° C.

Separation of the isomeric mixture:

Since the perfluorinated 1,3-dipiperidinopropane contained as the main component in the mixture, and its isomers, are difficult to separate from one another by distillation because of their equal molecular weights and consequently approximately equal boiling points, they were separated by fractional absorption on a gas chromatographic separating column filled with a zeolite molecular sieve with a pore size from 5 to 6 Å.

EXAMPLE 2

Analogously to the methods described in the foregoing example, the compounds of formula I listed in the following Table 1 were obtained by electrochemical perfluorination of corresponding starting compounds of formula II.

The structure of the compounds was verified by elemental analysis, NMR spectroscopy, IR spectroscopy, mass spectroscopy, and gas chromatography.

The oxygen dissolving capacity of the compounds of formula I given in Table 1 ($O_2$-solub.) was determined as follows:

The determination was performed in a two-liter round flask provided with a valve to deliver oxygen, a valve for evacuation, and a pressure gauge, and having a lower extension suitable for receiving the perfluorocarbon to be tested, into which the perfluorocarbon can be introduced through a septum.

The apparatus was first evacuated with a water-jet pump, filled with oxygen, again evacuated, and again filled with oxygen until an internal pressure of 1013 mbar was reached. Then the perfluorocarbon was introduced through a septum into the lower extension where it was stirred for 2 hours under an oxygen atmosphere. The temperature was held at 37° C. by means of a cryostat. After 2 hours a part of the perfluorocarbon was removed and tested for its oxygen content by gas chromatography.

The gas chromatography was performed with a CAP 12 gas chromatograph sold by Gira of France. The carrier gas was helium with a flow of 20 ml/min. The separating column was a glass column measuring 2 m ×4 mm in diameter, filled with 5 Å molecular sieve of 40–60 mesh. The oven temperature was 100° C; the injector temperature 250° C., and the detector temperature 200° C. The sample volume was 30 to 50 $\mu$l.

TABLE 1

| Example No. | Substance* Perfluoro- | Mol. Wt. | Boiling Point °C. | Yield | $O_2$** solub. vol. % 37° C. |
|---|---|---|---|---|---|
| 2 a | dimorpholinoethane | 560 | 162–166 MP 76° C. | 28% | 44 |
| 2 b | dimorpholinopropane | 610 | 181–183 MP 56° C. | 25% | 43 |
| 2 c | dimorpholinobutane | 660 | 196–200 | 30% | 41 |

TABLE 1-continued

| Example No. | Substance* Perfluoro- | Mol. Wt. | Boiling Point °C. | Yield | $O_2$** solub. vol. % 37° C. |
|---|---|---|---|---|---|
| 2 d | dimorpholinopentane | 710 | MP 65° C. 214–216 | 26% | 41 |
| 2 e | dimorpholinohexane | 760 | MP 60° C. 223–226 | 20% | 40 |
| 2 f | dimorpholinoheptane | 810 | MP 80° C. 238–243 | 21% | |
| 2 g | dimorpholinooctane | 860 | 250–253 | 14% | |
| 2 h | dipiperidinoethane | 628 | 181–189 | 26% | 43 |
| 2 i | dipiperidinopropane | 678 | 196–205 | 41% | 42 |
| 2 j | dipiperidinobutane | 728 | 210–217 | 22% | 42 |
| 2 k | dipiperidinopentane | 778 | 220–229 | 42% | 39 |
| 2 l | dipiperidinohexane | 828 | 235–239 | 15% | 38 |
| 2 m | dipiperidinoheptane | 878 | 260–273 | 12% | |
| 2 n | dipiperidinooctane | 928 | 278–290 | 9% | |

*Product obtained by distillation, contains no non-perfluorinated components, but may still contain small amounts of perfluorinated by-products
**Determined in each case for the pure chief product The starting compounds of formula II that were used were prepared in accordance with the following instructions:

A) Starting with a dihalide of formula V and a diamine of formula VI:

0.4 mol of diamine VI was heated together with 1.0 mol of dihalide V and 2.2 mol sodium carbonate in 300 ml of butanol for 6 hours at reflux temperature. Then the mixture was cooled and filtered, and the filtrate was concentrated with a rotary evaporator. The resulting compound of formula II was obtained from the concentrate by fractional distillation.

B) Starting with an amine of formula III and a compound of formula IV:

B1: 0.5 mol of a dichloroalkane compound of formula IV was heated together with 1 mole of an amine of formula III and 1.1 mole sodium carbonate in 200 ml butanol for 6 hours at reflux temperature. After the reaction mixture had cooled, the precipitated inorganic salts were filtered out and the filtrate concentrated on the rotary evaporator. The compound of formula II was then isolated from the concentrate by fractional distillation.

B2: To a solution of 3.2 mol of an amine of formula III in 300 ml of benzene, 0.8 mol of a dibromoalkane of formula IV was added drop by drop such that the solution remained at boiling. After it had been added the mixture was refluxed for one hour. Then the reaction mixture was cooled and filtered, and the filtrate concentrated by evaporation. The compound of formula II was obtained from the concentrate by fractional distillation.

C: Starting out with an amine of formula III and a diol of formula IV:

In an autoclave one mol of an amine of formula III and 0.4 mol of a diol of formula IV in 100 ml of dioxane were heated with 2 g of copper chromite under a hydrogen pressure of 100 atmospheres for 40 hours at 250° C. Then the reaction mixture was filtered and the compound of formula II was obtained from the filtrate by fractional distillation.

The following compounds of formula II, listed in Table 2, were prepared according to the above general instructions.

TABLE 2

| No. | Name of Substance | Prepared according to Instruction | Yield |
|---|---|---|---|
| A 1 | dimorpholinoethane | B I | 62% |
| | | A | 22% |
| A 2 | dimorpholinopropane | A | 42% |
| | | B I | 66% |
| | | B II | 77% |
| A 3 | dimorpholinobutane | B I | 40% |
| A 4 | dimorpholinopentane | A | 13% |
| | | B II | 46% |
| | | C | 14% |
| A 5 | dimorpholinoheptane | B II | 23% |
| A 6 | dimorpholinooctane | B II | 18% |
| A 7 | dimorpholinohexane | B II | 72% |
| A 8 | dipiperidinoethane | B I | 35% |
| | | B II | 30% |
| A 9 | dipiperidinopropane | B II | 89% |
| A 10 | dipiperidinobutane | B I | 18% |
| | | B II | 20% |
| A 11 | dipiperidinopentane | C | 10% |
| | | B II | 7% |
| A 12 | dipiperidinohexane | B II | 49% |
| A 13 | dipiperidinoheptane | B II | 26% |
| A 14 | dipiperidinooctane | B II | 17% |

EXAMPLE I:

Preparation of a stabilized aqueous emulsion containing perfluorodecalin.

2 g of perfluorodecalin and 0.1 g of perfluorodimorpholinobutane were added to 0.3 g of the emulsifier Pluronic ®F68 (= ethylene oxide/propylene oxide block polymer, average molecular weight 8300, Wyandotte Chemical) and water was added to the mixture to make a total volume of 10 ml. The mixture was homogenized for 2 minutes with an ultrasonic homogenizer (Labsonic ®2000 with standard probe, from Braun, Melsungen) at output 170. The resultant emulsion had an average colloid particle size of about 100–150 nm, which hardly increased at all when stored for several weeks at +4° C.

EXAMPLE II:

Aqueous emulsion containing an appropriate perfluorodecalin, suitable a blood substitute or perfusion medium.
Composition:
Perfluorodecalin: 190 g/l Perfluorodimorpholinobutane: 10 g/l
Emulsifier (Pluronic ®F68) 27 g/l
Glycerin: 8 g/l
Albumin phospholipids: 4 g/l
Hydroxyethyl starch (avg. molecular weight 200,000: 30 g/l
Na$^+$: 128.0 mmol/l
K$^-$: 4.5 mmol/l
Ca$^{++}$: 2.5 mmol/l
Mg$^{++}$: 2.1 mmol/l
Cl$^-$: 116.0 mmol/l
HCO$_3^-$: 25 mmol/l
Glucose: 10.0 mmol/l
Sterile distilled water to make: 1 liter The components listed above were homogenized in a conventional manner.

EXAMPLE III

Preparation of a stabilized aqueous emulsion containing perfluorocyclohexylmorpholine.

200 g of a mixture containing perfluorocyclohexylmorpholine and perfluoro-n-hexylmorpholine in a 2:1 ratio (prepared as in Example 1 by electrochemical fluorination of morpholinocyclohexene-(1) obtained by reacting morpholine with cyclohexanone; boiling point 147.5–148.5° C.) and 10 g of perfluorodimorpholinobutane were added to 35 g of the emulsifier egg yolk lecithin and water was added to the mixture to make a total volume of 1000 ml. The mixture was homogenized in a Model Lab 60/60 - 10 TBS made by Gaulin, at a pressure of 700 bar in 5 runs. The resulting emulsion had a colloid particle size of 100–150 nm which, when stored at +4° C. for several weeks increased hardly at all.

EXAMPLE IV

Comparison of the stability of an aqueous perfluorodecalin emulsion stabilized with perfluorodi-morpholinopropane, at various storage temperatures.

An emulsion of 20% (G/V) perfluorodecalin, 1% (G/V) perfluorodimorpholinopropane and 4% (G/V) emulsifier (Pluronic ®F 68) was prepared in water. For this purpose the components were homogenized for 2 minutes with an ultrasound homogenizer (Labsonic ®2000 with standard probe made by Braun of Melsungen) at output 170.

Then the average colloidal particle size was determined using an autosizer (Malvern Autosizer IIc with Automeasure Software Program 4.1). Then a part of the emulsion was stored at 6° C. and another part at 37° C. for 13 days, and the particle size determinations were performed repeatedly in both parts during the storage period. The results are given in the following table:

TABLE I

| Storage time T in days | Average colloidal particle size D in nm at storage temperature: | | Dt/Do | Dt/Do |
| --- | --- | --- | --- | --- |
| | 6° C. | 37° C. | 6° C. | 37° C. |
| 0 | 194.3 | 194.3 | 1 | 1 |
| 1 | 265.1 | 254.2 | 1.364 | 1.309 |
| 8 | 299.6 | 286.0 | 1.542 | 1.472 |
| 10 | 289.9 | 270.0 | 1.477 | 1.39 |
| 13 | 286.5 | 300.3 | 1.475 | 1.546 |

The foregoing description and examples have been set forth merely to illustrate the invention and are not intended to be limiting. Since modifications of the described embodiments incorporating the spirit and substance of the invention may occur to persons skilled in the art, the invention should be construed to embrace all variations within the scope of the appended claims and equivalents thereof.

What is claimed is:

1. A composition of matter suitable for preparing aqueous perfluorocarbon oil-in-water emulsions useful as oxygen carriers, said composition comprising, in admixture, a physiologically acceptable perfluorocarbon suitable for use as an oxygen carrier in a blood substitute, and an effective emulsion stabilizing amount of at least one perfluorinated heterocyclic compound corresponding to the formula I:

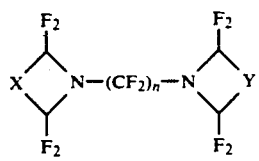

wherein
n represents an integer from 2 to 8;
X and Y represents a —CF$_2$—O—CF$_2$ group.

2. A composition of matter according to claim 1, wherein said perfluorocarbon is a heterto atom-containing perfluorocarbon.

3. A composition of matter according to claim 1, comprising from about 1 to about 20 weight-% of perfluorinated heterocyclic compound corresponding to the formula I.

4. A composition of matter according to claim 3, comprising from about 2.5 to about 10 weight-% of perfluorinated heterocyclic compound corresponding to the formula I.

5. A composition of matter according to claim 1, comprising a perfluorinated heterocyclic compound corresponding to the formula I wherein n represents an integer from 3 to 6.

6. A composition of matter according to claim 5, comprising a perfluorinated heterocyclic compound corresponding to the formula I wherein n represents 3 to 4.

7. A composition of matter according to claim 1, wherein said physiologically acceptable perfluorocarbon is a liquid at normal body temperature and has a boiling point in the range from about 130 t about 200° C.

8. A composition of matter according to claim 1, wherein said physiologically acceptable perfluorocarbon has a molecular weight in the range from about 450 to about 600.

9. A composition of matter according to claim 1, wherein said physiologically acceptable perfluorocarbon has a retention half-life in a human body in the range from about one week to about one month.

10. A composition of matter according to claim 1, wherein said physiologically acceptable perfluorocarbon comprises perfluorodecalin.

11. A composition of matter according to claim 1, wherein said physiologically acceptable perfluorocarbon comprises perfluoro-N-cyclohexylmorpholine.

12. A composition of matter according to claim 1, wherein said physiologically acceptable perfluorocarbon comprises a mixture of perfluoro-N-cyclohexylmorpholine and perfluoro-N-n-hexylmorpholine.

13. An aqueous perfluorocarbon oil-in-water emulsion comprising water, a physiologically acceptable perfluorocarbon suitable for use as an oxygen carrier in a blood substitute, and an effective emulsion stabilizing amount of at least one perfluorinated heterocyclic compound corresponding to the formula I:

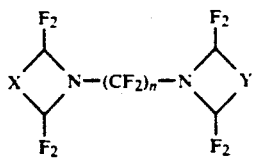

wherein n represents an integer from 2 to 8;

X and Y represents a —$CF_2$—O—$CF_2$— group, a —$CF_2$—$CF_2$—$CF_2$— group, or a —$CF(CF_3)$—$CF_2$— group, and Y represents a —$CF_2$—O—$CF_2$— group, a —$CF(CF_3)$—$CF_2$— group or a —$CF_2$—$CF_2$—$CF_2$— group.

14. An emulsion according to claim 13, wherein said physiologically acceptable perfluorocarbon is a hetero atom-containing perfluorocarbon.

15. An emulsion according to claim 13, further comprising a physiologically acceptable emulsifier.

16. An emulsion according to claim 13, containing from about 5 to about 50 grams of physiologically acceptable perfluorocarbon per 100 milliliters of emulsion.

17. An emulsion according to claim 16, containing from about 15 to about 25 grams of physiologically acceptable perfluorocarbon per 100 milliliters of emulsion.

18. An emulsion according to claim 13, containing a quantity of said perfluorinated heterocyclic compound corresponding to formula I in said emulsion which amounts to from 1 to 20 weight-% of the total quantity of said perfluorinated compound suitable for use as an oxygen carrier in a blood substitute and said perfluorinated heterocyclic compound corresponding to formula I.

19. An emulsion according to claim 18, containing a quantity of said perfluorinated heterocyclic compound corresponding to formula I in said emulsion which amounts to from 2.5 to 10 weight-% of the total quantity of said perfluorinated compound suitable for use as an oxygen carrier in a blood substitute and said perfluorinated heterocyclic compound corresponding to formula I.

20. A perfluorinated heterocyclic compound corresponding to the formula I':

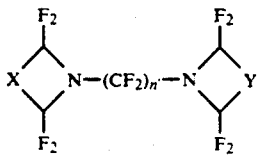

wherein n' represents an integer from 4 to 8;

X and Y represents a —$CF_2$—O—$CF_2$— group, a —$CF_2$—$CF_2$—$CF_2$— group, or a —$CF(CF_3)$—$CF_2$—0 group, and Y represents a —$CF_2$—O—$CF_2$— group, a —$CF(CF_3)$—$CF_2$— group or a —$CF_2$—$CF_2$—$CF_2$— group.

* * * * *